United States Patent [19]
Dinh

[11] Patent Number: 6,091,837
[45] Date of Patent: Jul. 18, 2000

[54] SENSOR FOR ACQUIRING A FINGERPRINT IMAGE BASED ON HEAT TRANSFER

[76] Inventor: Ngoc Minh Dinh, Anders Søysethsvei 8, H 14, N-7053 Ranheim, Norway

[21] Appl. No.: 08/930,787

[22] PCT Filed: Apr. 10, 1996

[86] PCT No.: PCT/NO96/00082

§ 371 Date: Oct. 6, 1997

§ 102(e) Date: Oct. 6, 1997

[87] PCT Pub. No.: WO96/32061

PCT Pub. Date: Oct. 17, 1996

[30] Foreign Application Priority Data

Apr. 11, 1995 [NO] Norway ................................. 951427

[51] Int. Cl.$^7$ ................................ G06K 9/28; G01B 7/34
[52] U.S. Cl. ............................ 382/124; 382/108; 374/43; 374/141
[58] Field of Search ................................. 382/124, 125, 382/126, 127, 108, 109, 115, 116, 137, 141, 312, 315; 702/130, 131, 133; 340/825.34; 374/43, 44, 141, 29, 31, 124, 164; 250/330, 318, 332, 339.04, 341.6, 352

[56] References Cited

U.S. PATENT DOCUMENTS

| | | | |
|---|---|---|---|
| 3,635,085 | 1/1972 | Shimotsuma et al. | 73/340 |
| 4,358,677 | 11/1982 | Ruell et al. | 250/216 |
| 4,429,413 | 1/1984 | Edwards | 382/4 |
| 4,582,985 | 4/1986 | Lofberg | 235/380 |
| 4,866,276 | 9/1989 | Leavens et al. | 250/341 |
| 4,978,230 | 12/1990 | Adiutori et al. | 374/43 |
| 5,108,193 | 4/1992 | Furubayashi | 374/164 |
| 5,302,022 | 4/1994 | Huang et al. | 374/44 |
| 5,897,610 | 4/1999 | Jensen | 702/134 |

FOREIGN PATENT DOCUMENTS 8203286 9/1982 WIPO.

*Primary Examiner*—Leo H. Boudreau
*Assistant Examiner*—Brian P. Werner
*Attorney, Agent, or Firm*—Rothwell, Figg, Ernst & Kurz, P.C.

[57] ABSTRACT

A method and apparatus is provided for measuring patterns in an at least partially heat conducting surface. The method includes the steps of bringing a plurality of surface sensor elements into thermal contact with a substantial part of a surface to be examined, heating the plurality of surface sensor elements with a supplied heat, measuring a temperature or a change in temperature of each surface sensor element one or more times, or continuously, comparing the measured temperature or the change in temperature in each surface sensor element to the supplied heat to provide a measure of a loss of heat from each surface sensor element to the surface to be examined, and collocating the loss of heat at each surface sensor element to provide a segmented picture of the surface to be examined based upon a variation in the loss of heat from the plurality of surface sensor elements.

10 Claims, 3 Drawing Sheets

SENSOR FOR ACQUIRING A FINGERPRINT IMAGE BASED ON HEAT TRANSFER

This application is a National Stage Filing under 35U.S.C. 371 of International application PCT/NO96/00082, filed on April 10, 1996 and published as WO 96/32061 on Oct. 17, 1996.

SENSOR FOR ACQUIRING A FINGERPRINT IMAGE BASED ON HEAT TRANSFER

The invention relates to a method and an apparatus for measuring patterns in a partially heat conducting surface, preferably a fingerprint.

Identification by the use of fingerprints has lately come to the fore as a result of the increasing danger of the forging of credit cards, as well as the greatly increased availability of pattern recognition algorithms. Some systems for recognition of fingerprints have already been made available on the market. The technique used to register the fingerprint varies.

Some of the previously known solutions are based upon optical technology using light with one or more wavelengths. These are sensitive to dirt and contamination, both in the fingerprint and on the sensor surface, and thus cleaning is necessary for both.

Another alternative is pressure measurements. This, however, has the disadvantage that the sensor surface becomes sensitive to mechanical wear and damage, as the sensor has to have an at least partially compliant surface.

Since these kind of sensors may be exposed to long term use in varying and sometimes demanding conditions the sensor needs to have a robust surface, to be as insensitive to pollution in the fingerprint and on the sensor as possible, and to be able to be screened electrically in order to avoid interference from outside and electromagnetic discharges that can harm the electronic circuits in the sensor. It must be capable of reading most fingerprints without being disturbed by latent prints from earlier use. It must also be capable of reading worn fingerprints in which the pattern is no longer visible. In some cases, e.g. in credit cards, it would also be advantageous if the sensor could be made compact.

In the view of costs there is also a demand for simplicity and minimizing of the number of parts.

An interesting alternative is to measure the pattern in the fingerprint using the difference in temperature between the "valleys" and the "ridges". This, however, demands very sensitive detectors, and is also sensitive regarding variations in temperature due to different circumstances. This kind of sensors is known from Norwegian patent 153,193 (corresponding to U.S. Pat. No. 4,582,193 and U.S. Pat. No. 4,429,413.

It is an object of the present invention to provide a sensor being easy to produce, making them cheap in production, and also having such small dimensions that they may be integrated in identification cards and credit cards or the like. It is an additional object to make a sensor being as insensitive to pollution in the fingerprint and on the sensor as possible, and which may be used without maintenance for long periods of time.

According to the present invention the problems related to the known solutions are solved using a method as being characterized in claim 1, and a sensor device as defined in claim 7.

The invention is related to detection of thermal structures by measuring differences in heat conductivity at the surface, preferably a fingerprint, touching the sensor. This makes the measurements independent of the temperature of the surroundings.

Dirt and contamination will be less critical for the measurements of the sensor than in other, corresponding methods. If a relatively smooth, thin layer of contamination is present on the sensor it will, to a certain degree, affect the contrast in the picture, but the print may still be read. Larger quantities of dirt affecting the measured heat conduction may give measuring errors.

The heat conductivity is measured by heating the sensor being touched by the object to be measured, and by measuring the resulting change in temperature (relative temperature) in relation to the provided energy. The better heat conductivity the measured object has, the less the local change in temperature will be. The heat conductivity can be measured as a function of time, integrated over a period of time or at a chosen time after the heating is started or stopped. A plurality of measurements, or a continuous temperature control at each measuring element, provides a possibility for calculating the heat capacity as well as providing a measurement of the heat conductivity in the measured object.

The heating in itself may be performed in different ways. Joint heating of the whole sensor is one possibility. To obtain a joint heating, the heat generated in other electronic circuits coupled to the sensor may be used.

In a preferred embodiment of the invention a separate heat source is used at each separate temperature sensor, which provides a controlled and accurate measurement in each point, so that the method and apparatus is less sensitive to local variations in temperature. This is also advantageous since the provided energy may be controlled at each temperature sensor, which gives an improved control of the temperature, and since the energy sources may be positioned close to the surface and the object to be measured, and thus gives less use of energy and faster response since the mass to be heated is closer.

The invention will be described in detail referring to the disclosed drawings.

Figure 1:
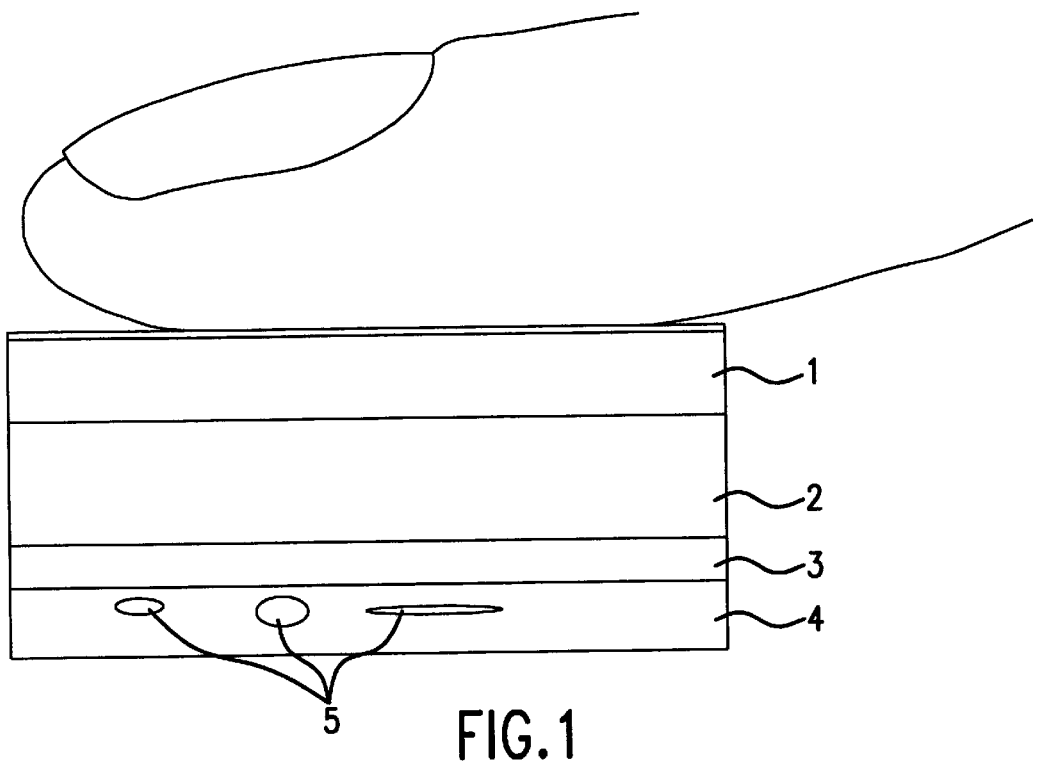
FIG. 1 shows a schematic cross section of the position of the sensor system.

In FIG. 1 a schematic view of the position of the sensor in relation to the other circuits is shown. The sensor 1 is directly in contact with the fingerprint. The system circuits 4 are provided, among other things, to control and manage the collection of data from the sensor 1. Underneath the sensor 1 a layer may be provided of a thermally insulating, or partially insulating, material 2 in order to limit the heat conduction to and from the other electronic system circuits 4. To enhance the insulation the layer may be provided with a cavity under each sensor element. If the heat from the system circuits 4 is to be used in the measurements of the heat conduction this layer may be made thinner.

Between the system circuits 4 and the insulation layer 2 a heat conducting layer 3 is shown that provides a uniform distribution of heat from the different system circuits 5 on the sensor. This way smooth and accurate measurements are secured.

The physical thickness of the sensors will vary, but when used in relation to, or mounted on, identification cards the thickness will preferably be as small as possible, preferably less than 0.5 mm comprising the system circuits 5.

The most interesting materials for use in the sensor are the following. The electronic circuits are made from semiconducting materials, preferably with well known silicon, or gallium arsenide (GaAs) technology, and electric and thermal insulation is provided by using $SiO_2$ or other materials permitting direct mounting of semiconducting materials. The electric conductors are preferably made from aluminum, or from gold or other materials common in relation to semiconductors. An alternative may be using polymer based semiconductors, conductors and insulating materials, which would be advantageous in relation to credit and identification cards, as they provide a large degree of pliancy and elasticity.

Figure 2:
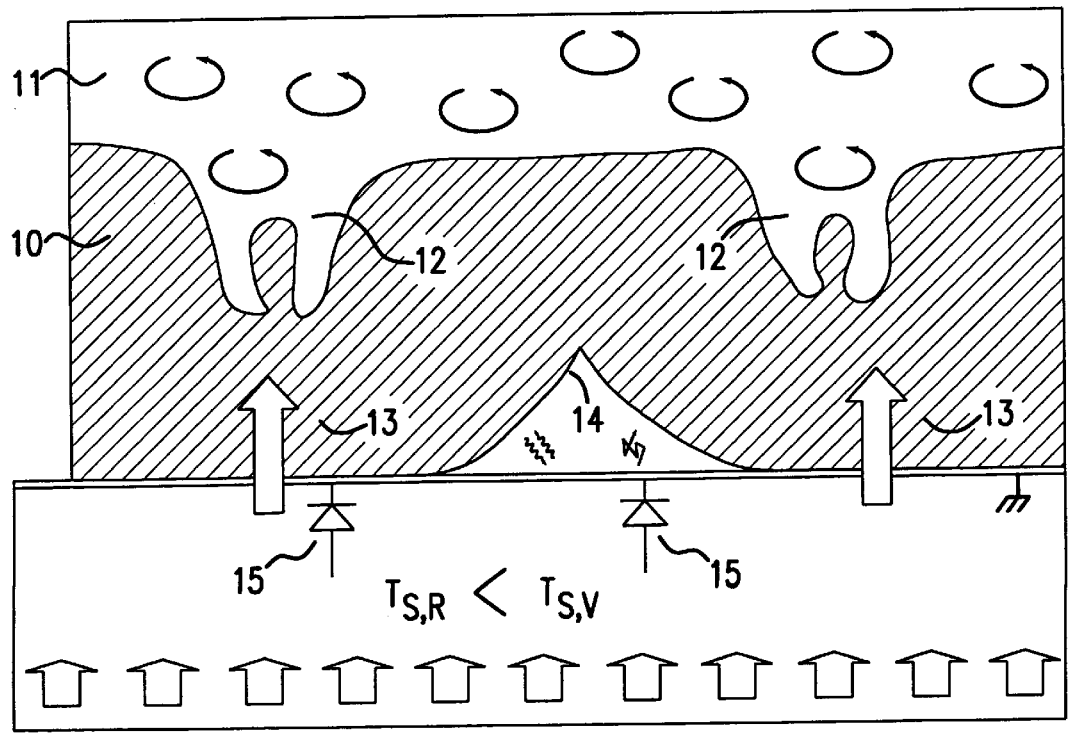
FIG. 2 shows a detail of the contact surface between the fingerprint and the sensor.

FIG. 2 shows a detail of the contact surface between the sensor and the fingerprint in which the sensor is heated by means of a uniform heat supply indicated by arrows in the sensor. The fingerprint comprises ridges 13 with valleys 14 between them. The skin is comprised by an outer skin 10 (epidermis) with an area 11 behind it with circulation of blood (indicated by circular arrows). Underneath the ridges 13 there are papilla 12 which, among other things have blood circulation. The ridges 13 come in contact with the sensor and are heated, and the blood circulation in the finger transports the heat away. In the valleys the surface of the sensor is cooled essentially by two mechanisms, radiation and heat conduction in the air comprised in the valley 14. These cooling mechanisms are not as efficient as the heat conduction in the ridges 13, which results in a difference between the relative temperature $T_{s,r}$, measured in the ridges 13 and the relative temperature $T_{s,v}$, which is not. These temperatures may be measured using the temperature sensors 15. Measurements from all the temperature sensors 15 are collected and, using information regarding supplied energy, a pattern is made showing the fingerprint.

The temperature at the temperature sensors 15 may be measured at one or more points of time, or continuously. Using a plurality of, or continuous, measurements a picture may be obtained showing the effective heat capacity at the different measuring points, in addition to the heat conductivity. Since the sweat ducts 8 and the surrounding skin cells 9 (sweat diffusion), which due to a high content of water have a high heat capacity, is comprised in the ridges of a fingerprint, the difference in heat capacity will enhance the ability of the sensor to distinguish the ridges from the valleys.

Because the sensors measure the temperature the output signal from one sensor is essentially inversely proportional to the heat conduction at the measured point in the fingerprint. A collocation of these signals will therefore provide a pattern indicating the distribution of heat conductivity, and thus the fingerprint.

To begin with the temperature sensor 15 will be a conventional electronic component, but it is clear that other measuring techniques, e.g. optical or acoustic, may be utilized.

The contrast in the measured fingerprint may be enhanced by increasing the supplied heat. Because of the difference in heat conductivity the areas that do not have the heat transported away will increase their temperature faster than the other areas. This provides a direct method for increasing the contrast in the signal without the use of picture manipulation or other extensive calculations.

Figure 3:
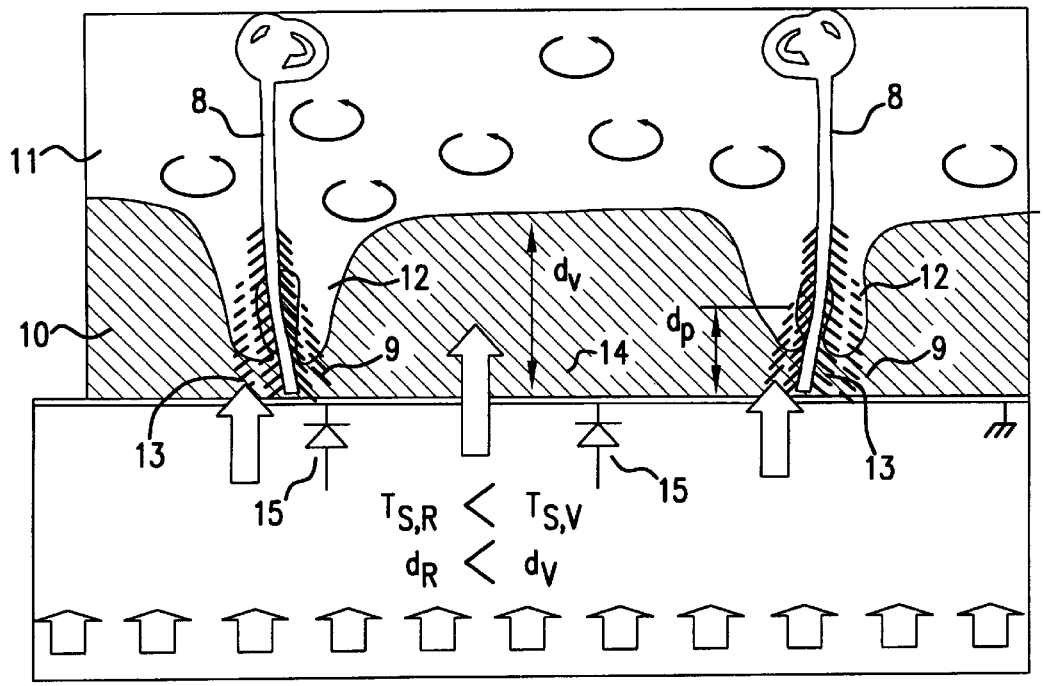
FIG. 3 shows the same situation as FIG. 2, but with a worn fingerprint.

FIG. 3 shows a corresponding situation where the ridges in the fingerprint are worn off, and thus the fingerprint is not actually visible. The difference in heat conductivity is here given by the thickness of the outer skin 10. By the previous ridges 13 an increase in heat conductivity compared to the previous valleys 14 may still be measured. This is because the distance from the sensor to the area with blood circulation, because of the papilla, is less than the distance $d_v$ in the valley areas 14. The supplied heat in the ridge areas is thus transported more efficiently away than the supplied heat in the valley areas. Therefore this kind of fingerprints may also be registered by difference in heat conductivity, in addition to the difference in effective heat capacity.

Figure 4:
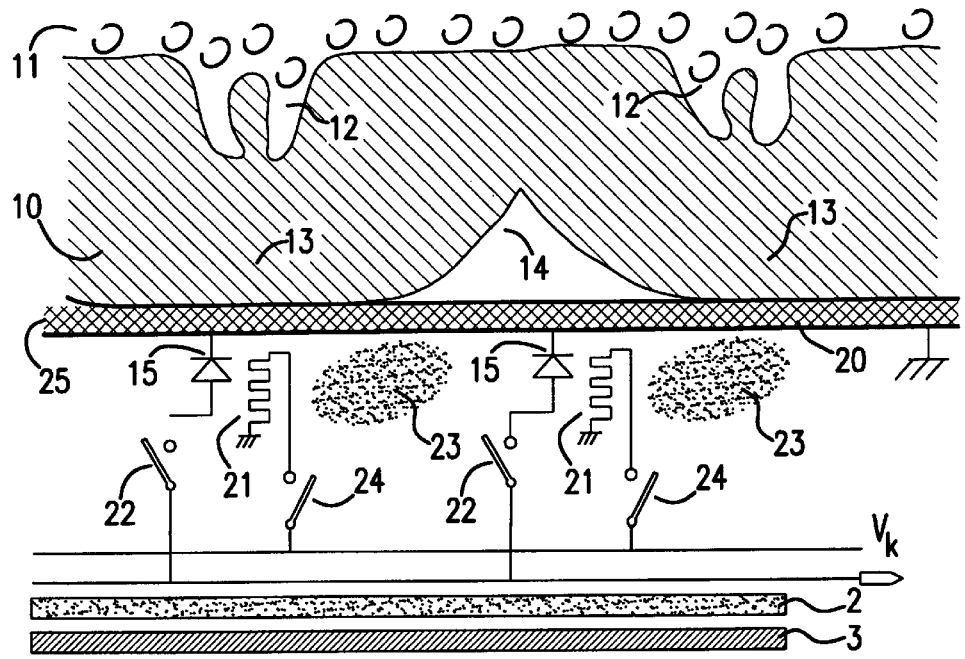
FIG. 4 shows essentially the same as FIG. 2, but with a sketch of the electronic circuits connected to the sensor.

FIG. 4 shows a schematic sketch of a possible layout of the electronic circuits of the sensor. Closest to the fingerprint an electrically conducting, earthed layer 20 is drawn, made e.g. from aluminum or other conducting or semiconducting materials, to avoid electric disturbances from the surroundings and to prevent discharges from harming the sensor. This layer 20 may also comprise a layer made from a mechanically resistant material 25, e.g. $SiO_2$, $Si_3N_4$ or $\alpha$-$Al_2O_3$, to protect the sensor from mechanical stress and chemical corrosion. These layers 20,25 should preferably be sufficiently thin as not to hinder the heat transportation to the fingerprint and affect the measurements.

Between the sensor elements 15 there is an insulating area 23 limiting the heat conduction between the elements. In practice the sensor elements 15 will be surrounded by insulating areas in order to thermally insulate them from each other. There is, however, an interesting embodiment within the scope of the invention in which a certain degree of heat conduction is permitted between the sensor elements 15. This may provide a filtering effect which, among other things, suppresses the effect of unwanted local variations in temperature, i.e. reducing noise in the picture, without the use of extensive calculations.

Heat conduction between the elements may be chosen in many ways, e.g. by the physical dimensions and the shape of the insulating area, in choosing materials or by regulating the thickness of the electrically conducting layer 20 to let the heat be transported in it.

By the combination of an increase in the supplied heat and an allowed, controlled heat conduction between the sensor elements, the contrast may be maintained while smoothing the signal.

The insulating area may for example be made from $SiO_2$ or similar materials. A preferred embodiment from a production point of view would be that the insulating material is the same as, or compatible with, and is connected to, the thermal insulating layer 2 in FIG. 1. Choosing a material permitting an integrated production of the electronic circuits would also be beneficial in the manufacturing process.

Each sensor element 15 in the shown example has a corresponding heating element 21 producing a known amount of heat. In the shown example the heating elements 21 are controlled centrally by $V_k$ and by using an electronic contact switch 24. It is, however, possible to provide the circuit with a separate control of each heating element to give a local control of the heat supply. A possible technique in achieving this is described below. The signal from the temperature sensor is addressed and controlled using an electronic contact switch 22, e.g. a double gate MosFET transistor.

Figure 5:
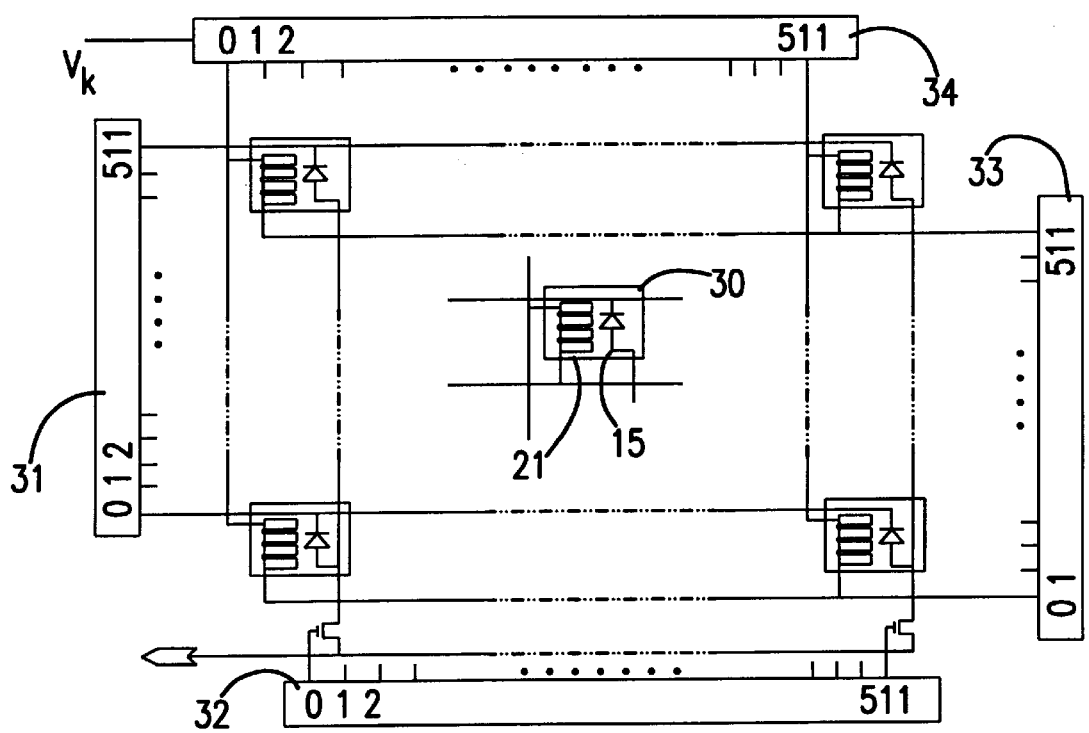
FIG. 5 shows a schematic view of the temperature sensor circuit.

In FIG. 5 a schematic sketch of the circuit of temperature sensors is shown. In the shown example the sensor is comprised by 512×512 sensor units 30 corresponding to one pixel in previously mentioned segmented picture, and which may be read separately or simultaneously in groups in a conventional manner. The physical size of the sensor may vary according to the fingerprint to be measured, but starting at approximatly 13×13 mm². The pixel size must be sufficiently small to provide a picture of the structure of the fingerprint. Using the above mentioned dimensions the pixels will have the size of approximately 25.4×25.4 $\mu$m². The sensor is integrally made with common semiconductor technology, or possibly with polymer technology.

The row and column registers 31,32 may be provided as a part of the sensor or as a part of the system circuits, and may be used for collecting data from, and addressing of, the separate pixels.

The row and column registers 33,34 may be comprised by the sensor or by the system circuits and may be used in addressing and controlling each of the heating elements.

To achieve a controlled, local heating of each sensor element the pixel of interest may be addressed repeatedly, possibly with a regulation of the access time. Thus a current is repeatedly sent through the electronic circuit of the sensor element. This will result in an accumulated heating of the sensor element which may be used in a partial control of the heat supply in the chosen pixel.

The sensor is described above in relation to the measuring of fingerprints. It is, however, clear that it also may be used on other surfaces with a varying heat conductivity, heat capacity and/or thermic structures in the surface. An example might for instance be measuring of structures in bank notes or similar structured surfaces. The sensor may also be used in inspecting inhomogeneities close to a surface, such as cracks and irregularities in materials as long as they affect the heat conduction of the measured object.

I claim:

1. A method for measuring fingerprint patterns, comprising the steps of:

bringing a plurality of surface sensor elements into thermal contact with a substantial part of a finger surface to be examined, heating the plurality of surface sensor elements with a supplied heat, measuring a temperature or a change in temperature of each surface sensor element one or more times, or continuously, comparing the measured temperature or the change in temperature in each surface sensor element to the supplied heat to provide a measure of a loss of heat from each surface sensor element to the finger surface to be examined, and collocating the loss of heat at each surface sensor element to provide a segmented picture of the finger surface to be examined based upon a variation in the loss of heat from the plurality of surface sensor elements.

2. The method according to claim 1, wherein the measurement at each surface sensor element is controlled and read separately.

3. The method according to claim 1, wherein the heating of each surface sensor element is controlled separately by addressing a local temperature sensor in a surface sensor element of interest, so that the local temperature sensor behaves as a heat source.

4. The method according to claim 1, wherein the plurality of surface sensor elements are partially thermally insulated using an insulating material, and that the heat transfer of the insulating material contributes in smoothing the differences in temperature or damping the changes in temperature between the plurality of surface sensor elements to provide a filtering effect in the segmented picture.

5. The method according to claim 1, wherein a contrast in the segmented picture is enhanced by increasing the heat supplied to the surface elements in general or to each surface sensor element individually.

6. The method according to claim 5, wherein each surface sensor element is heated individually and the heat supplied to each surface sensor element is adjusted according to the temperature, or the change in temperature, of each surface sensor element.

7. An apparatus for measuring fingerprint patterns, comprising:

a plurality of sensor elements adapted to thermal contact with a substantial part of a finger surface to be examined, a plurality of temperature sensors adapted for measuring a temperature or a change in temperature of each surface sensor element of said plurality of surface sensor elements, at least one heating device adapted for heating said plurality of surface sensor elements by providing a supplied heat, and a means for generating a signal corresponding to heat transfer at each surface sensor element based upon the supplied heat and on the measured temperature or the change in temperature, wherein said signal corresponding to each said surface sensor element is used to establish an overall, segmented picture of the finger surface to be examined based upon a difference in heat loss at each said surface sensor element of said plurality of surface sensor elements.

8. The apparatus according to claim 7, wherein said apparatus further includes a partially thermally insulating material between the plurality of surface sensor elements.

9. The apparatus according to claim 7, wherein each surface sensor element is provided with a separate heat source.

10. The apparatus according to claim 7, wherein each surface sensor element is adapted to at least partially control the heat supply.

* * * * *